US009440985B2

(12) United States Patent
Zapolsky et al.

(10) Patent No.: US 9,440,985 B2
(45) Date of Patent: Sep. 13, 2016

(54) TRICYCLIC DERIVATIVES OF N,N'-SUBSTITUTED 3,7-DIAZABICYCLO [3.3.1]NONANES AND DRUGS BASED THEREON

(76) Inventors: Maxim Eduardovich Zapolsky, Tomilino (RU); Nikolay Serafimovich Zefirov, Moscow (RU); Vladimir Alexandrovich Palyulin, Moscow (RU); Mstislav Igorevich Lavrov, Moscow (RU)

( * ) Notice: Subject to any disclaimer, the term of this patent is extended or adjusted under 35 U.S.C. 154(b) by 272 days.

(21) Appl. No.: 14/110,432

(22) PCT Filed: Apr. 2, 2012

(86) PCT No.: PCT/RU2012/000239
§ 371 (c)(1),
(2), (4) Date: Apr. 13, 2015

(87) PCT Pub. No.: WO2012/138255
PCT Pub. Date: Oct. 11, 2012

(65) Prior Publication Data
US 2015/0274743 A1    Oct. 1, 2015

(30) Foreign Application Priority Data
Apr. 6, 2011 (RU) ................. 2011113043

(51) Int. Cl.
*A61K 31/425* (2006.01)
*C07D 487/18* (2006.01)
*C07D 255/04* (2006.01)
*C07D 417/12* (2006.01)

(52) U.S. Cl.
CPC ........... *C07D 487/18* (2013.01); *C07D 255/04* (2013.01); *C07D 417/12* (2013.01)

(58) Field of Classification Search
None
See application file for complete search history.

(56) References Cited

FOREIGN PATENT DOCUMENTS

| RU | 1045592 A | 10/1995 |
| RU | 1107541 A | 10/1995 |
| RU | 2333211 C1 | 9/2008 |
| RU | 2417082 A2 | 1/2011 |
| WO | 2011006653 A1 | 1/2011 |

OTHER PUBLICATIONS

Adam Doble / The Role of Excitotoxicity in Neurodegenerative Disease: Implications for Therapy // Pharmacology and Theraputics. 1999. V. 81, N 3, pp. 163-221.
Daniel T. Monaghan, Deborah Yao and Carl W. Cotman / Distribution of [pH] AMPA binding sites in rat brain as determined by quantitative autoradiography // Brain Res., 1984, V. 324, pp. 160-164.
Amy Arai and Gary Lynch / Factors regulating the magnitude of long-term potentiationinduced by theta pattern stimulation // Brain Res., 1992. V. 598, pp. 173-184.
H. Lassmann, R. Weiler, P. Fischer, C. Bancher, K. Jellinger, E. Floor, W. Danielczyk, F. Seitelberger and H. Winkler / Synaptic pathology in alzheimer's disease: immunological data for markers of synaptic and large dense-core vesicles // Neuroscience, 1992, V. 46, pp. 1-6.
Richard Granger, Ursula Staubli, Mike Dams, Yael Perez, Lena Nilsson, Gary A. Rogers, And Gary Lynch / A Drug That Facilitates Glutamatergic Transmission Reduces Exploratory Activity and Improves Performance in a Learning Dependent Task // Synapse, 1993, V. 15, pp. 326-329.
Amy Arai a, Markus Kessier, Peng Xiao, Jos Ambros-Ingerson , Gary Rogers, Gary Lynch // A centrally active drug that modulates AMPA receptor gated currents // Brain Res., 1994, V. 638, pp. 343-346.
I. Ito, S. Tanabel, A. Kohda and H. Sugiyama / Allosteric potentiation of quisqualate receptors by a Nootropic drug aniracetam // J. PhysioL, 1990, V. 424, pp. 533-543.
U. Staubli, M. Kessler, G.Lynch / Aniracetam has proportionately smaller effects on synapses expressing long-term potentiation: Evidence that receptor changes subserve LTP // Psychobiology, 1990, 18(4), pp. 377-381.
Peng Xiao, Ursula Staubli, Markus Kessier, and Gary Lynch / Selective Effects of Aniracetam Across Receptor Types and Forms of Synaptic Facilitation in Hippocampus // Hippocampus, 1991, V. 1, pp. 373-380.
A. Guenzi and M. Zanetti / Determination of aniracetam and its main metabolite, N-anisoyl-GABA, in human plasma by high-performance liquid chromatography // J. Chromatogr., 1990, V. 530, pp. 397-406.
Ursula Staubli, Yael Perez, Fangbo Xu, Gary Rogerstt, Martin Ingvar, Sharon Stone-Elander and Gary Lynch / Centrally active modulators of glutamate receptors facilitate the induction of long-term potentiation in vivo // PNAS, 1994, V. 91 pp. 11158-11162.

(Continued)

*Primary Examiner* — Heidi Reese
(74) *Attorney, Agent, or Firm* — Arent Fox LLP; Michael Fainberg (57) ABSTRACT

The invention relates to novel 3,6,9-triazatricyclo[7.3.1.1] tetradecane-4,8,12-trione derivatives of general formula (1), which act as allosteric AMPA receptor modulators, and to drugs based thereon which can be used for treating Alzheimer's, Parkinson's and other neurodegenerative diseases.

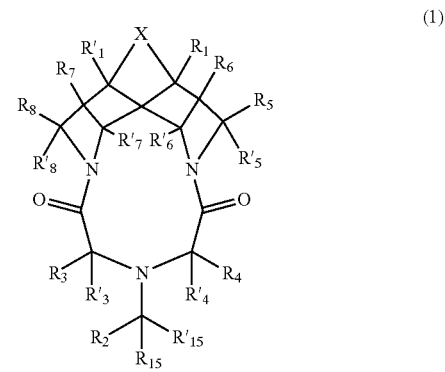

(HM)

13 Claims, 7 Drawing Sheets

(56) References Cited

OTHER PUBLICATIONS

B. Legutko, X. Li, P. Skolnick / Regulation of BDNF expression in primary neuron culture by LY392098, a novel AMPA receptor potentiator // Neuropharmacology, 2001, V. 40, pp. 1019-1027.

M. Ebadi, R. M. Bashir, M. L. Heidrick, F. M. Hamada, H. El Refaey, A. Hamed, G. Helal, M. D. Baxi, D. R. Cerutis and N. K. Lassi / Neurotrophins and their receptors in nerve Injury and repain eurochemistry International // Neurochem Int., 1997, V. 30, pp. 347-374.

Judith A. Siuciak, C. Anthony Allar, Stanley J. Wiegand, Roland M. Lindsay / Antinociceptive effect of brain-derived neurotrophic factor and neurotrophin-3 // Brain Research, 1994, V. 633, pp. 326-330.

Michiko Ono, Junji Ichihara, Takeshi Nonomura, Yasushi Itakura, Mutsuo Taiji, Chikao Nakayama, and Hiroshi Noguchi / Brain-Derived Neurotrophia Factor Reduces Blood Glucose Level in Obese Diabetic Mice but Not in Normal Mice // Biochem. and Bioph. Res. Commun., 1997, V. 238, pp. 633-637.

Brian Villumsen Broberg, Birte Yding Glenthøøj, Rebecca Dias, Dorrit Bjerg Larsen, Christina Kurre Olsen / Reversal of cognitive deficits by an ampakine (CX516) and sertindole in two animal models of schizophrenia—sub-chronic and early postnatal PCP treatment in attentional set-shifting // Psychopharmacology, 2009, V. 206, pp. 631-640.

Danielle A. Simmons, Christopher S. Rex, Linda Palmer, Vijay Pandyarajan, Vadim Fedulov, Christine M. Gall, and Gary Lynch // Up-regulating BDNF with an ampakine rescues synaptic plasticity and memory in Huntington's disease knockin mice // Proc. Natl. Acad. Sci. USA, 2009, V. 106, pp. 4906-4911.

Toshiharu Shimazaki, Ayaka Kaku, Shigeyuki Chaki // Blockade of the metabotropic glutamate 2/3 receptors enhances social memory via AMPA receptor in rats // Eur J Pharmacol., 2007, V. 575, pp. 94-97.

Donald C Golf, J Steven Lamberti, Andrew C Leon, Michael F Green, Alexander L Miller, Jayendra Patel, Theo Manschreck, Oliver Freudenreich and Steven A Johnson / A Placebo-Controlled Add-On Trial of the Ampakine, CX516, for Cognitive Deficits in Schizophrenia // Neuropsychopharmacology, 2008, V. 33, pp. 465-472.

TRICYCLIC DERIVATIVES OF N,N'-SUBSTITUTED 3,7-DIAZABICYCLO [3.3.1]NONANES AND DRUGS BASED THEREON

This application is a National Stage entry of International Application No. PCT/RU2012/000239, filed on Apr. 2, 2012, which claims priority to and the benefit of Russian Application No. 2011113043, filed on Apr. 6, 2011. The entire content of these prior applications is incorporated herein by reference.

FIELD

This invention relates generally to novel derivatives of N,N'-substituted diazabicyclononanes which are potentially capable of allosteric modulation of AMPA (2-amino-3-(3-hydroxy-5-methylisoxazol-4-yl)propionic acid) receptors. More specifically, the present invention relates to novel derivatives of N,N'-substituted 3,7-diazabicyclo-[3.3.1] nonanes having pharmacological activity and which may be employed for the treatment of neurodegenerative pathologies. The present invention also relates to medicaments containing said compounds.

PRIOR ART

The glutamatergic system, to which the AMPA receptors belong, is a primary excitatory neuromediator system in the brain of mammals, including humans, and participates in the implementation of a whole series of physiological and pathological processes. It is known that a wide range of psycho-neurological illnesses, such as Parkinson's disease (PD), Alzheimer's disease (AD) and similar neurodegenerative disorders, is associated with disruption of the regulation of these processes [Doble A. Pharmacology and Therapeutics, 1999, 81, (3), 163-221].

AMPA receptors are unevenly distributed in the brain. A high concentration of these receptors was found in the superficial layers of the neocortex and in the hippocampus [Monaghan, Brain Res., 1984, 324, 160-164]. Studies in animals and man have shown that these structures are mainly responsible for sensomotor processes and are a matrix for highly behavioral reactions. Signals in the neurological networks of the brain, responsible for the combination of cognitive processes, are thus transmitted due to AMPA receptors.

For the reasons set out above, drugs which enhance the functioning of AMPA receptors participate in the regulation of processes which form memory, and also processes responsible for the recovery of nerve cells. It has been demonstrated in experiments [Arai, Brain Res., 1992, 598, 173-184] that enhancing the AMPA-mediated synaptic response function increases induction of long-term potentiation (LTP). There is much evidence that LTP, reflecting an increase in the strength of synaptic contacts, which ensures constant physiological activity in the brain, is the physiological basis of memory and learning processes. For example, substances which block LTP hinder memory mechanisms in animals and humans [Cerro, Neuroscience, 1992, 46, 1-6]. Substances which enhance the function of AMPA receptors, promoting LTP induction, can favorably influence cognitive function [Granger, Synapse, 1993, 15, 326-329; Arai, Brain Res., 638, 343-346].

Many compounds which activate AMPA receptors are now known. Aniracetam may be taken as an example [Ito, J. Physiol., 1990, 424, 533-543]. It was demonstrated that aniracetam enhances the synaptic signal at several hippocampus sites, while having no effect on NMDA-mediated signals [Staubli, 1990, Psychobiology, 18, 377-381; Xiao, Hippocampus, 1991, 1, 373-380]. One of the features of this preparation is that its effect is short-term. When used peripherally, it is converted into anisoyl-GABA (about 80% of the drug), which no longer has any aniracetam-like effects [Guenzi, J. Chromatogr., 1990, 530, 397-406]. The clinical effect of aniracetam is manifested only when it is used in high concentrations (0.1 mM).

A class of substances which in their physiological effect are allosteric modulators of AMPA receptors, was discovered comparatively recently. These compounds are more stable and more effective than those previously known, as has been demonstrated in experiments [Staubli, PNAS, 1994, 91, 11158-11162].

In connection with the rapid development of research related to investigation of the pharmacological effect of similar compounds, the experimental fact has recently been established that the intense ionic current which is induced by the action of such allosteric modulators on AMPA receptors, with subsequent depolarization of the post-synaptic membrane, triggers the mechanism of expression of genes responsible for the synthesis of the neurotrophins NGF (nerve growth factor) and BDNF (brain-derived neurotrophic factor)—neural tissue growth factors [Legutko B., Neuropharmacology, 2001, 40, 1019-1027; Ebadi, Neurochemistry International, 2000, 30, 347-374]. The process of expression of genes responsible for neurotrophin synthesis is of enormous importance in the treatment of neurodegenerative disorders and other psycho-neurological diseases. Thus, BDNF has been shown to have an antidepressant effect in behavioral models [Siuciak, Brain Research, 1994, 633, 326-330] and to reduce the blood glucose concentration in mice suffering from diabetes [Ono, J. Biochem. and Bioph. Res. Commun., 1997, 238, 633-637].

In contrast to known stimulants (caffeine, methylphenidate (Ritalin) and amphetamine), ampakines do not elicit such long-term side-effects as insomnia, and are being studied actively as a potential drug to treat brain diseases such as Alzheimer's disease, Parkinson's disease, schizophrenia and other neurological and neurodegenerative disorders. For example, Broberg B. V. et al. (Psychopharmacology, 2004, Apr. 24) demonstrated improvement in cognitive status in schizophrenia when using AMPAkine CX516, while Simmons D. D. et al. (Proc. Natl Acad. Sci. USA, 2009, Mar. 24; 106 (12), 4906-11) established a positive change in cognitive status in Huntington's disease in animal models.

Shimazaki T. et al. (Eur. J. Pharmacol., 2007 Dec. 1; 575, (1-3), 94-7), in an experiment on adult rats, established that compound CX546 in a concentration of 0.3-3 mg/kg improves social memory specifically thanks to positive stimulation of AMPA receptors.

Compound CX516 has become one of the few which have been studied in human patients as a treatment supplementary to antipsychotics in schizophrenia (Goff D. C. et al., Neuropsychopharmacology, 2008 February; 33 (3), 456-72). And although the authors did not observe a significant improvement in the general condition of the patients or in their cognitive status as compared with placebo, they were certain that the search for new and more selective products in this category should be continued.

DISCLOSURE OF THE INVENTION

The invention now proposed is aimed at solving the task of expanding the arsenal of agents which can be employed as novel effective allosteric modulators of AMPA receptors.

As a result of studies performed to search for such compounds, including those triggering the mechanism of expression of genes responsible for the synthesis of neurotrophins—neural tissue growth factors, particularly among compounds having similar activity, the inventors have discovered a broad group of novel derivatives of N,N'-substituted 3,7-diazabicyclo[3.3.1]nonanes in the form of free bases and salts with pharmacologically acceptable acids, which are together characterized in detail below and constitute one of the aspects of the present invention.

The technical result of the present invention is the creation of novel tricyclic derivatives of N,N'-substituted 3,7-diazabicyclo[3.3.1]nonanes, including the bases and salts thereof with pharmacologically acceptable acids, which in combination are represented by general formula (1):

(HM)

wherein:

HM here and hereinafter denotes a pharmacologically acceptable acid;

X is a carbonyl group, a methylene group or OH;

$R_1$ and $R'_1$ may be the same or different, and each independently is H, $C_1$-$C_6$alkyl or $C_1$-$C_{10}$alkoxy;

$R_2$ in combination is represented by general formulae (1.1a), (1.2a), (1.3a), (1.4a):

1.1a 1.2a 1.3a 1.4a

$R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, $R'_{10}$, $R_{11}$, $R'_{11}$, $R_{15}$ and $R'_{15}$ may be the same or different and each independently is H, $C_1$-$C_6$alkyl or $C_1$-$C_{10}$alkoxy;

$R_{12}$ is $C_1$-$C_6$alkyl;

$R_{13}$ and $R_{13}'$ may be the same or different and each independently is H, $C_1$-$C_6$alkyl, $C_1$-$C_{10}$alkoxy, hydroxy, halogen, amino, nitro group, nitrile, acyl or aryl;

Z is N or CH;

E is N, or a group with the general formula:

wherein: n=1-3; $R_{14}$ is H, $C_1$-$C_6$alkyl, $C_1$-$C_{10}$alkoxy or hydroxyl;

Y is —$(CR_{16}R'_{16})_m$—, wherein m=1-3;

$R_{16}$ and $R'_{16}$ may be the same or different and each independently is H, $C_1$-$C_6$alkyl, or $C_1$-$C_{10}$alkoxy;

The term "halogen" which is here employed means fluorine, chlorine, bromine or iodine.

The term "alkoxy" means an AlkO— group. Examples of alkoxy groups include methoxy, butoxy, isopropyloxy and similar groups.

The term "acyl" means a C(O)R group (in which R signifies H, alkyl or aryl as defined above). Examples of acyl groups include formyl, acetyl, benzoyl, phenylacetyl and similar groups.

The term "aryl" signifies an unsubstituted or substituted phenyl or naphthyl group. The substituents of a phenyl group may be halogens (such as fluorine, chlorine and similar), lower alkyl groups (such as methyl, ethyl, isopropyl and similar), or lower alkoxy groups (such as methoxy, ethoxy, isopropoxy and similar). The substituents of a naphthyl group may be fluorine, chlorine, bromine, methyl and methoxy groups.

The term "amino" signifies an NR'R" group (in which R' and R" may be the same or different, and each independently is H, alkyl, cycloalkyl or aryl, as defined above). Examples of an amino group include diisopropylamine, diphenylamine, methylethylamine, etc.

The term "pharmacologically acceptable acids" encompasses all pharmacologically acceptable acids, both inorganic (such as hydrochloric, sulfuric, phosphoric, etc.), and organic (such as formic, acetic, oxalic, citric, tartaric, maleic, succinic, p-toluenesulfonic, methylsulfuric, etc.).

PREFERRED EXEMPLARY EMBODIMENT OF THE INVENTION

Among the compounds of formula (1) which constitute the subject of the present invention, the following three groups of compounds, which can be represented by formulae (1.1), (1.2), (1.3) and (1.4) shown below, are preferred. The following compounds are particularly preferred:

1.1. N,N'-substituted 3,7-diazabicyclo[3.3.1]nonanes of general formula (1.1):

(HM)

1.2. N,N'-substituted 3,7-diazabicyclo[3.3.1]nonanes of general formula (1.2):

(HM)

1.3. N,N'-substituted 3,7-diazabicyclo[3.3.1]nonanes of general formula (1.3):

(HM)

1.4. N,N'-substituted 3,7-diazabicyclo[3.3.1]nonanes of general formula (1.4):

(HM)

wherein:
HM here and hereinafter is a pharmacologically acceptable acid;
E, Z, $R_1$, $R_3$, $R_3'$, $R_4$, $R_4'$, X, Y, $R_5$, $R_5'$, $R_6$, $R_6'$, $R_7$, $R_7'$, $R_8$, $R_8'$, $R_9$, $R_9'$, $R_{10}$, $R_{10}'$, $R_{11}$, $R_{11}'$, $R_{12}$, $R_{13}$, $R_{13}'$, $R_{15}$ and $R_{15}'$ have the meanings specified above for formula 1.

The most preferred compounds of formula 1.1 (in the form of pharmacologically acceptable salts and/or the free bases) are:
6-[4-methoxy-3-(1H-pyrazol-1-ylmethyl)benzyl]-1,11-dimethyl-3,6,9-triazatricyclo[7.3.1.1]tetradecane-4,8,12-trione,
6-[4-methoxy-3-(3,5-dimethyl-1H-pyrazol-1-ylmethyl)-benzyl]-1,11-dimethyl-3,6,9-triazatricyclo[7.3.1.1]tetradecane-4,8,12-trione,
6-[4-methoxy-3-(2-methyl-1H-pyrazol-1-ylmethyl)benzyl]-1,11-dimethyl-3,6,9-triazatricyclo[7.3.1.1]tetradecane-4,8,12-trione.

The most preferred compound of formula 1.2 (in the form of pharmacologically acceptable salts and/or the free bases) is:
6-[4-methoxy-3-(piperidin-1-ylmethyl)benzyl]-1,11-dimethyl-3,6,9-triazatricyclo[7.3.1.1]tetradecane-4,8,12-trione.

The most preferred compound of formula 1.3 (in the form of pharmacologically acceptable salts and/or the free bases) is:

6-{3-[(2-fluorophenoxy)methyl]-4-methoxybenzyl}-1,11-dimethyl-3,6,9-triazatricyclo[7.3.1.1]tetradecane-4,8,12-trione.

The most preferred compound of formula 1.4 (in the form of pharmacologically acceptable salts and/or the free bases) is:

6-{4-methoxy-3-[(1,3-thiazol-2-ylamino)methyl]benzyl}-1,11-dimethyl-3,6,9-triazatricyclo[7.3.1.1]tetradecane-4,8,12-trione.

The invention is described in more detail below with the aid of examples of the preparation of particular compounds.

The starting reagents, and also the final products, are prepared by methods known in the literature or are commercially available.

A Scheme for the Synthesis of the Final Compounds is Presented Below:

Scheme 1:

where R' is a halogen, and $R_{15}$ and $R_{15}'$ have the meanings specified above for formula 1.

The structures of the compounds prepared were confirmed by the results of chemical and spectral analyses and other physico-chemical characteristics.

The examples given below illustrate but do not limit this invention.

Example 1

6-[4-methoxy-3-(1H-pyrazol-1-ylmethyl)benzyl]-1,11-dimethyl-3,6,9-triazatricyclo[7.3.1.1]tetradecane-4,8,12-trione White crystals, yield 84%

PMR spectrum (CDCl$_3$ δ, ppm): 1.0 (s, 3H), 1.1 (s, 3H), 2.7 (d, J=13.3, 2H), 3.0 (d, J=13.3, 2H), 3.2 (d, J=14.1, 2H), 3.5 (s, 2H), 3.7 (d, J=14.1, 2H), 3.9 (s, 3H), 4.9 (m, 4H), 5.3 (s, 2H), 6.26 (s, 1H), 6.9 (d, J=8.4, 1H), 7.0 (s, 1H), 7.3 (d, J=8.4, 1H), 7.45 (s, 1H), 7.49 (s, 1H)

Example 2

6-[4-methoxy-3-(3,5-dimethyl-1H-pyrazol-1-ylmethyl)-benzyl]-1,11-dimethyl-3,6,9-triazatricyclo[7.3.1.1]tetradecane-4,8,12-trione White crystals, yield 80%

PMR spectrum (CDCl$_3$ δ, ppm): 1.0 (s, 3H), 1.1 (s, 3H), 2.15 (s, 3H), 2.2 (s, 3H), 2.7 (d, J=13.3, 2H), 3.0 (d, J=13.3, 2H), 3.2 (d, J=14.1, 2H), 3.5 (s, 2H), 3.7 (d, J=14.1, 2H), 3.9 (s, 3H), 4.9 (m, 4H), 5.3 (s, 2H), 6.26 (s, 1H), 6.9 (d, J=8.4, 1H), 7.0 (s, 1H), 7.3 (d, J=8.4, 1H)

Example 3

6-[4-methoxy-3-(piperidin-1-ylmethyl)benzyl]-1,11-dimethyl-3,6,9-triazatricyclo[7.3.1.1]tetradecane-4,8,12-trione White crystals, yield 76%.

PMR spectrum (CDCl$_3$ δ, ppm): 1.0 (s, 3H), 1.2 (s, 3H), 1.45-1.53 (m, 6H), 2.47 (br.s, 4H), 2.7 (d, J=13.3, 2H), 3.0 (d, J=13.3, 2H), 3.2 (d, J=14.1, 2H), 3.5 (s, 2H), 3.58 (s, 2H), 3.7 (d, J=14.1, 2H), 3.9 (s, 3H), 4.9 (m, 4H), 6.9 (d, J=8.4, 1H), 7.2 (d, J=8.4, 1H), 7.4 (s, 1H)

Example 4

6-{3-[(2-fluorophenoxy)methyl]-4-methoxybenzyl}-1,11-dimethyl-3,6,9-triazatricyclo[7.3.1.1]tetradecane-4,8,12-trione White crystals, yield 88%

PMR spectrum (CDCl$_3$ δ, ppm): 1.0 (s, 3H), 1.1 (s, 3H), 2.7 (d, J=13.3, 2H), 3.0 (d, J=13.3, 2H), 3.2 (d, J=14.1, 2H), 3.5 (s, 2H), 3.7 (d, J=14.1, 2H), 3.9 (s, 3H), 4.9 (m, 4H), 5.3 (s, 2H), 6.9-7.18 (m, 5H), 7.3 (d, J=8.4, 1H), 7.45 (s, 1H), 7.53 (s, 1H)

Example 5

6-[4-methoxy-3-(2-methyl-1H-pyrazol-1-ylmethyl)benzyl]-1,11-dimethyl-3,6,9-triazatricyclo[7.3.1.1]tetradecane-4,8,12-trione White crystals, yield 74%

PMR spectrum (CDCl$_3$ δ, ppm): 1.0 (s, 3H), 1.1 (s, 3H), 2.45 (s, 3H), 2.7 (d, J=13.3, 2H), 3.0 (d, J=13.3, 2H), 3.2 (d, J=14.1, 2H), 3.5 (s, 2H), 3.7 (d, J=14.1, 2H), 3.9 (s, 3H), 4.9 (m, 4H), 5.1 (s, 2H), 6.7 (s, 1H), 6.8 (s, 1H), 6.95 (d, J=8.4, 1H), 7.0 (s, 1H), 7.2 (d, J=8.4, 1H)

Example 6

6-{4-methoxy-3-[(1,3-thiazol-2-ylamino)methyl]benzyl}-1,11-dimethyl-3,6,9-triazatricyclo[7.3.1.1]tetradecane-4,8,12-trione White crystals, yield 75%

PMR spectrum (CDCl$_3$ δ, ppm): 1.0 (s, 3H), 1.1 (s, 3H), 2.7 (d, J=13.3, 2H), 3.0 (d, J=13.3, 2H), 3.2 (d, J=14.1, 2H), 3.5 (s, 2H), 3.7 (d, J=14.1, 2H), 3.9 (s, 3H), 4.9 (m, 4H), 5.3

(s, 2H), 6.46 (d, J=3.2, 1H), 6.8 (d, J=3.2, 1H), 6.9 (d, J=8.4, 1H), 7.0 (s, 1H), 7.3 (d, J=8.4, 1H), 7.45 (s, 1H), 7.49 (s, 1H)

A Study of the Effects of Compounds of General Formula 1 on Learning in a "Weak" Model of Passive Avoidance in Chicks Methods The method of one-trial passive avoidance conditioning of chicks (*Gallus gallas domesticus*) aged 1-3 days was used to study the effect of the compound on the memory of animals. The advantage of the model is the rapid conditioning, which permits accurate recording of conditioning time and which leads to formation of long-term memory. The unossified skull of chicks allows pharmacological preparations to be administered with a micro-syringe directly into specified brain structures without operation and anesthesia; systemic administration of preparations is also employed, this being facilitated by the immature blood-brain barrier.

Animals. "Ptichnoye" crossbred chicks (male) were used in the experiments. The chicks were delivered from a chicken farm on the day of hatching and were kept in pairs in cages measuring 20×25×20 with constant access to water and food, at a temperature of 28° C. with a light cycle of 12:12 hours. The minimum time for adaptation to the situation before commencing an experiment was two hours.

Injections. The test compounds were dissolved in physiological saline and administered to the animals at various times before and after conditioning. Intra-cranial injections were given bilaterally using 10 µl micro-syringes (Hamilton) using a plastic head restrainer and were directed into the region of the lateral ventricles of the brain. The injection volume was 5 µl per hemisphere. After completing the experiment and decapitating the animals, the surface of the skull and brain were checked to determine the location of the injections. Intraperitoneal injections in a volume of 0.1 ml were used for systemic administration of the solutions. Control animals in all the experiments were given injections of the same volume of physiological saline.

The "weak" conditioning model.

Conditioning chicks using the "weak" model of passive avoidance leads to the formation of selective avoidance of the aversive object (a bead), which is retained for a period of 6-12 hours after conditioning; avoidance is not observed in most of the conditioned animals when tested after 24 hours. The experiments were performed using the following protocol: preliminary conditioning, consisting of sequential presentation to each animal of two neutral (wetted with water) beads fixed to a rod, was carried out 20 min. before conditioning. Only those chicks which pecked each bead at least once in the course of the first 10 s were used for further conditioning. An "aversive" bead, wetted with a pungent substance (10% solution of methyl anthranilate in ethanol) was presented to the chicks for conditioning. Chicks which had pecked the bead demonstrated the typical species-specific aversion reaction. Testing was carried out hours after conditioning and comprised a 10-second presentation of exactly the same, but dry, "aversive" bead as during conditioning, and then a neutral bead. A selective reaction of avoidance of the "aversive" bead was assessed as the presence of a long-term memory. The percentage of animals which demonstrated the avoidance reaction in the various experimental groups was compared in order to assess the memory level; the statistical reliability of the differences was assessed using the non-parametric $\chi^2$ test.

Results

Figure 1:
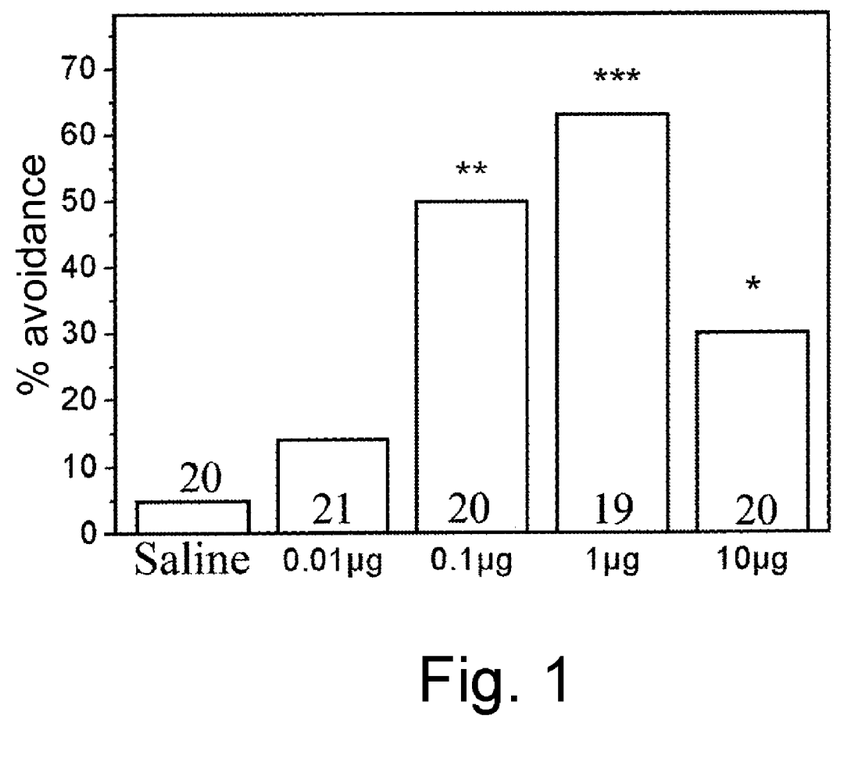
FIG. 1—results of test with intra-cerebral administration (into lateral ventricles, 5 μl per hemisphere) of experimental substance 5 min. before conditioning. 24 hours test.

1. Intra-cerebral injection of the experimental substance 5 min. before conditioning (into the lateral ventricles, 5 µl per hemisphere). 24 h test. *$p<0.05$; $p<0.01$; *$p<0.001$ compared with the control (saline). The results of the test are presented in FIG. 1.

Figure 2:
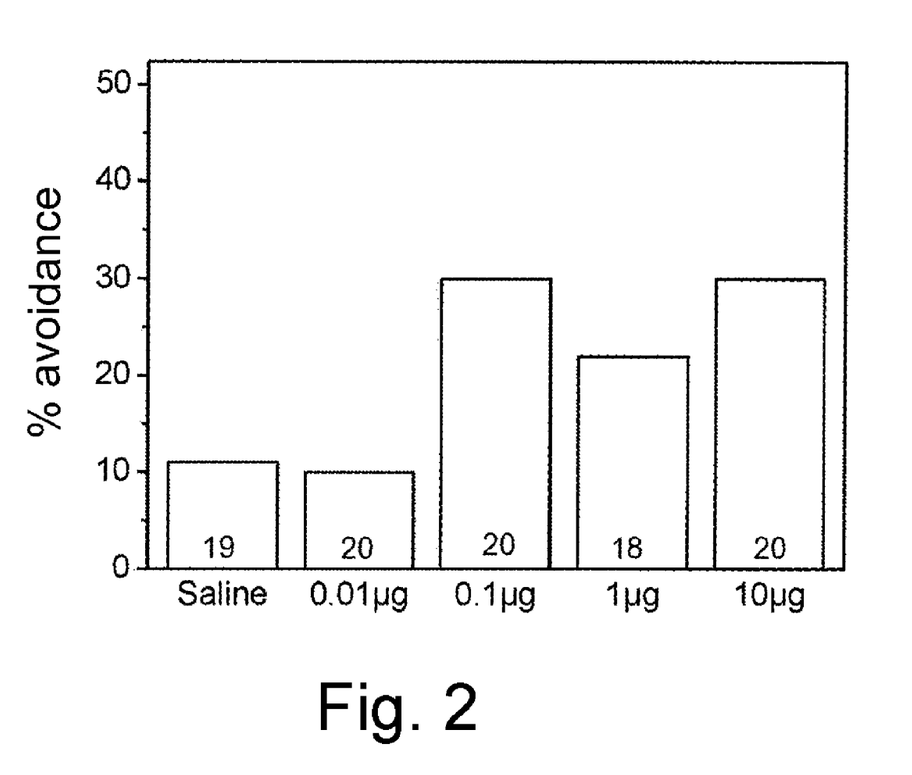
FIG. 2—results of test with intra-cerebral administration (into lateral ventricles, 5 μl per hemisphere) of experimental substance 30 min. before conditioning. 24 hours test.

2. Intra-cerebral injection of the experimental substance 30 min. before conditioning (into the lateral ventricles, 5 µl per hemisphere). 24 h test. No reliable differences between the groups. Results—see FIG. 2.

Figure 3:
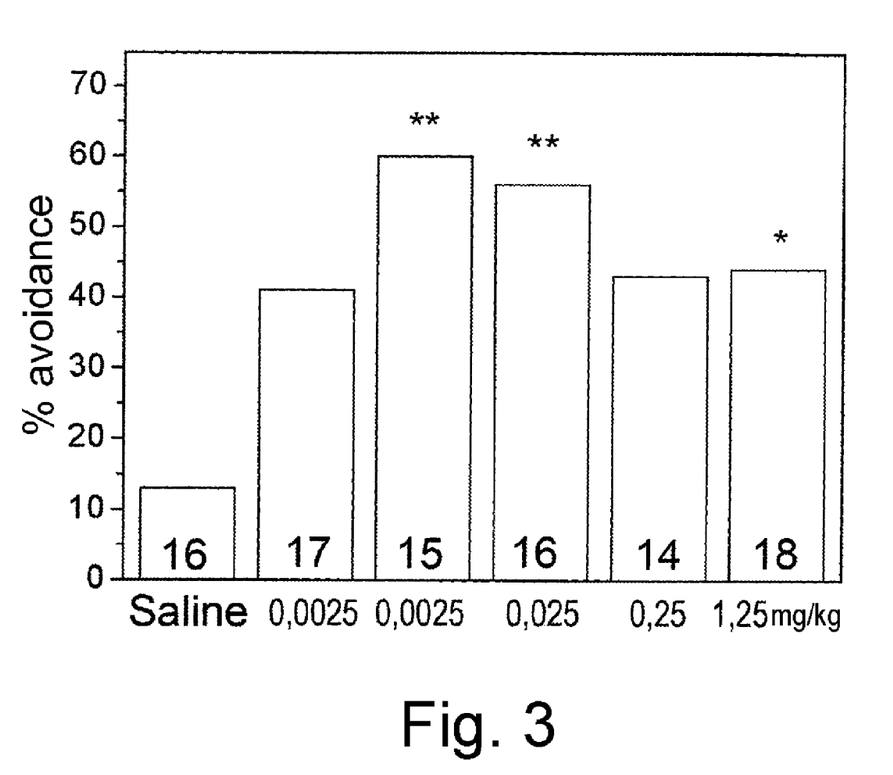
FIG. 3—results of test with systemic administration (intra-peritoneally, 0.1 ml) of experimental substance 10 min. before conditioning. Doses employed correspond to the range 0.01-50 μg per animal. 24 hours test.

3. Systemic injection of the experimental substance 10 min. before conditioning (intra-peritoneally, 0.1 ml). The doses employed correspond to a range of 0.01-50 µg per animal. 24 hour test. *$p<0.05$; $p<0.01$ compared with the control (saline). Results—see FIG. 3**.

Figure 4:
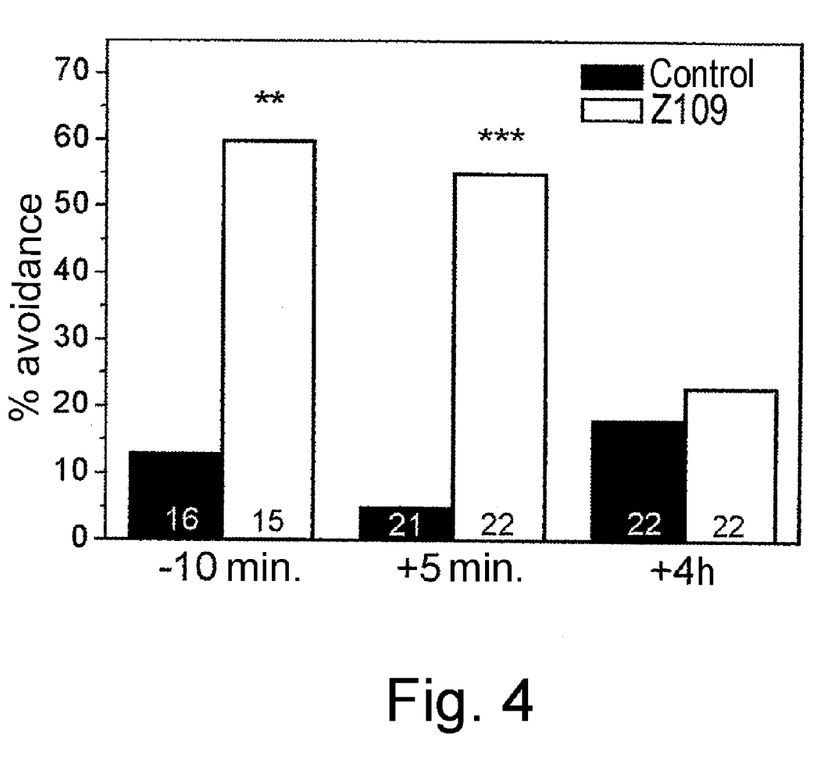
FIG. 4—results of test with systemic administration (intra-peritoneally, 0.1 ml) of 0.0025 mg/kg of experimental substance 10 min. before, or 5 minutes or 4 hours after, conditioning. Dose employed corresponds to 0.1 μg per animal. 24 hours test.

4. Systemic injection of experimental substance at 0.0025 mg/kg 10 min. before conditioning, and 5 min. or 4 hours after conditioning (intra-peritoneally, 0.1 ml). The dose employed corresponds to 0.1 µg per animal. 24 hours test. $p<0.01$; *$p<0.001$ compared with the control. Results—see FIG. 4.

Figure 5:
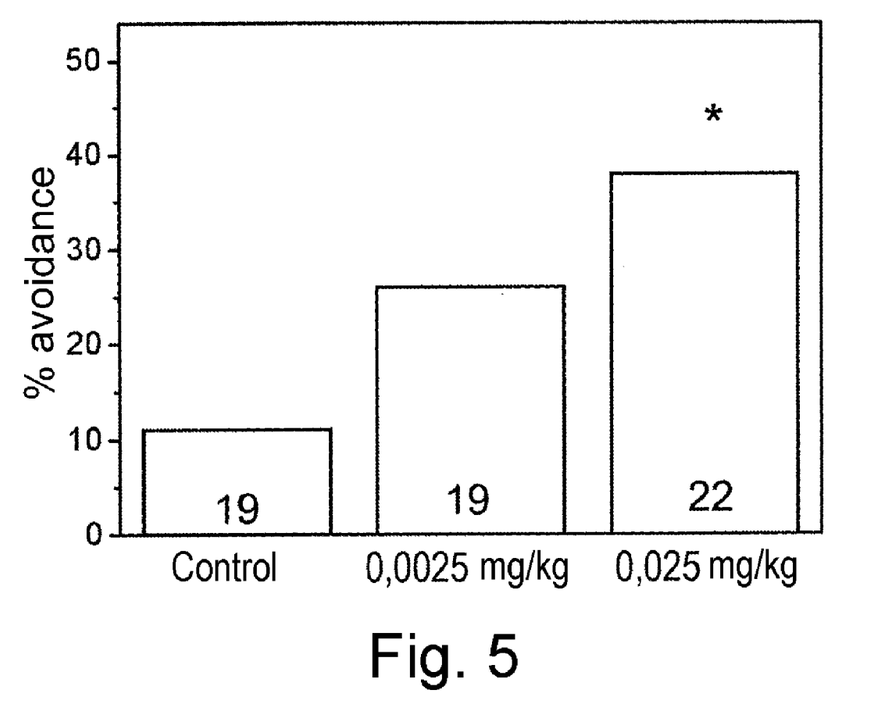
FIG. 5—results of test with peroral administration of experimental substance 10 min. before conditioning (0.0025 mg/kg and 0.025 mg/kg, in a volume of 0.1 ml; corresponds to 0.1 and 1 μg per animal).

5. Peroral administration of the experimental substance 10 min. before conditioning (0.0025 mg/kg and 0.025 mg/kg, in a volume of 0.1 ml; corresponds to 0.1 and 1 µg per animal). *$p<0.05$ compared with the control. Results—see FIG. 5.

A Study of the Effect of a Compound of General Formula 1 on Conditioning in a "Weak" Model of Conditioned Reflex Freezing in Mice Methods C57 B1/6 mice were placed in a chamber with an electrode floor for 60 seconds, and 5 seconds after placing on the electrode floor a 0.16 mA current was delivered for 2 seconds. The mice were tested after 24 hours by placing in the same chamber for three minutes. The percentage of the test time during which the animals were stationary (frozen) was shown on a graph. This time is an indication that the animals remember said context as dangerous.

Experiment 1

Figure 6:
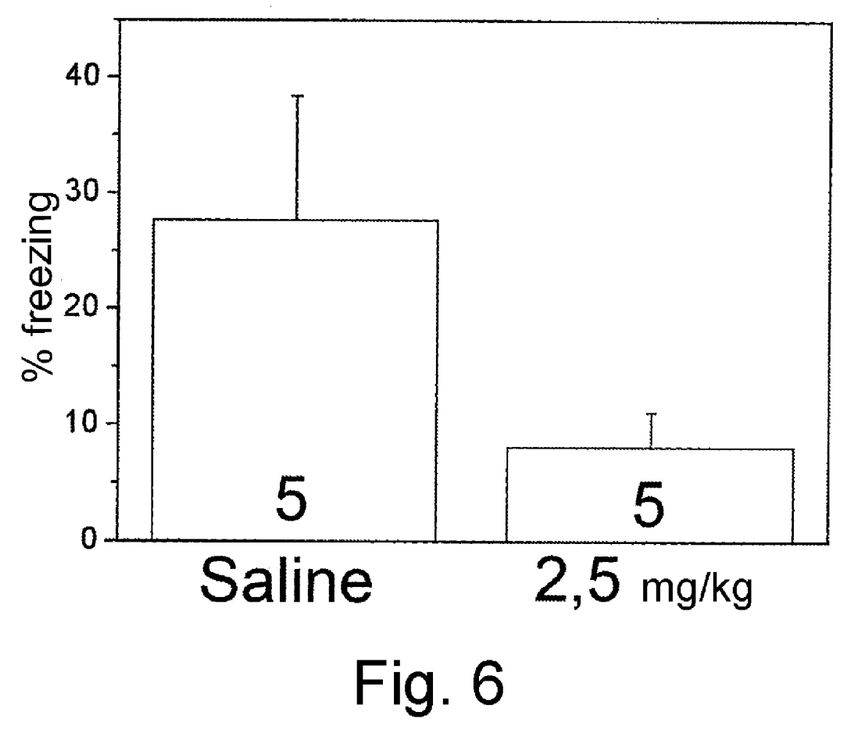
FIG. 6—results of test with intra-peritoneal administration of substance of general formula 1 in a dose of 2.5 mg/kg 15 minutes before conditioning.

Before the experiment, the mice were kept in standard laboratory cages with 5 mice per cage. A substance of general formula 1 was injected intra-peritoneally (0.1 ml per 10 g of weight) in a dose of 2.5 mg/kg, 15 minutes before conditioning. In this dose, the experimental substance reduced the freezing percentage in conditioned animals. The results are presented in FIG. 6.

Experiment 2

Figure 7:
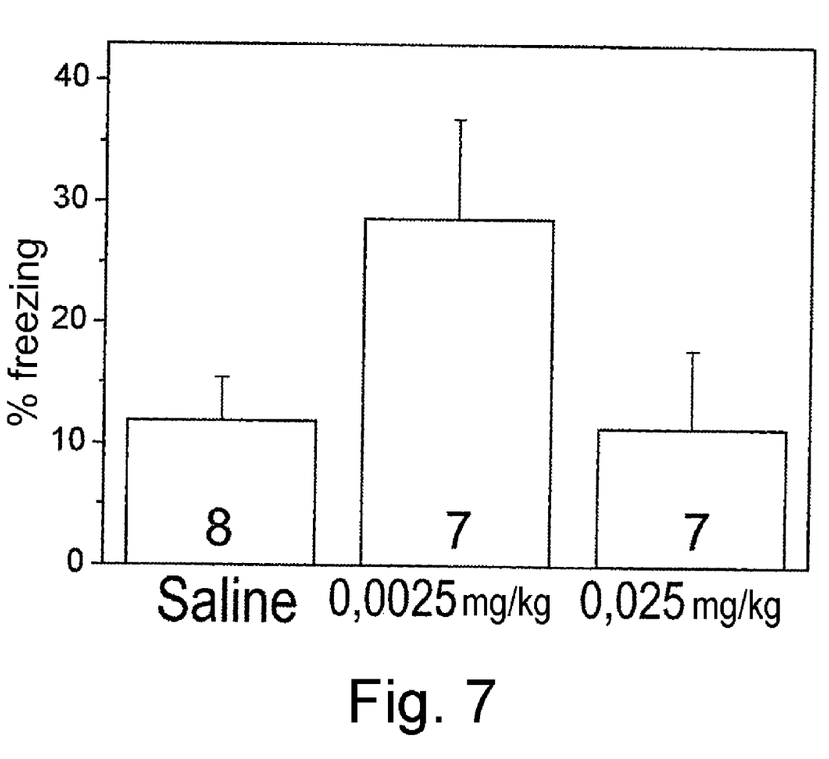
FIG. 7—results of test with intra-peritoneal administration of experimental substance in a dose of 0.0025 mg/kg and in a dose of 0.025 mg/kg 15 minutes before conditioning.

22 C57 B1/6 mice were used. Before the experiment, the mice were kept in standard laboratory cages with 5 mice per cage. The experimental substance was injected intra-peritoneally (0.1 ml per 10 g of weight) in a dose of 0.0025 mg/kg and in a dose of 0.025 mg/kg, 15 minutes before conditioning. Conditioning and testing were carried out in the same manner as in the previous experiment. The results are presented in FIG. 7.

Summary

1. Systemic (intra-peritoneal) administration of the experimental substance in a dose of 0.0025 mg/kg 10-15 minutes before "weak" conditioning led to the formation of a stable memory in mice and chicks. When tested 24 hours after conditioning, the animals of the experimental group (administration of the experimental substance) demonstrated a reliably higher level of reproduction of the learned response than did the animals of the control group.

2. The effect of enhancement of the "weak" memory was also observed in chicks when the experimental substance was administered 5 minutes after conditioning, but not 4 hours after conditioning, which suggests that the preparation acts on cellular processes occurring in the first few minutes after conditioning.

3. Intra-cerebral administration of the experimental substance in doses of 0.1 and 1 μg 5 minutes before conditioning led to a reliably higher level of reproduction of the learned response when tested after 24 hours. Administration of the preparation 30 minutes before conditioning was ineffective, which may be associated with the rapid metabolism thereof.

4. Peroral administration of the experimental substance to chicks in a dose of 0.025 mg/kg 10 minutes before conditioning led to a reliably higher level of reproduction of the learned response when tested after 24 hours.

5. Intra-peritoneal administration of the experimental substance to mice in a high dose (2.5 mg/kg) not only did not enhance the memory, but led to a reliable fall in the freezing level in the test. Chicks also exhibited a tendency for the cognitive-stimulating effect to decrease when higher doses of the preparation (10 μg for intra-cerebral and 0.25-1.25 mg/kg for intra-peritoneal administration) were used.

The experiments performed thus permit the following conclusion to be drawn.

The experimental substance exhibits a cognitive-stimulating effect in "weak" conditioning models in chicks and mice when administered directly before or immediately after conditioning; it can be assimilated from the gastro-intestinal tract and pass through the blood-brain barrier; it is effective in low doses; when the dose is increased the effect is reduced or reversed.

Report on a Study of the Nootropic Activity of Compounds of General Formula 1 in a Model of Amnesia Caused by Electric Shock Using the Passive Avoidance Conditioned Reflex Investigational Methods The investigations were carried out using a method of assessing development of a passive avoidance conditioned reflex (PACR). Amnesia was modeled using ECS in animals with a developed avoidance reflex. Testing was carried out 2 and 24 hours after conditioning.

Principles of the Methods Employed:

PACR

The investigations were performed on previously selected animals with a developed "exploratory" reflex in conditions of food deprivation for 24 hours before the investigation.

The selection of animals for testing was carried out in a special box consisting of a dark section and a light section. An animal was placed in the light section of the box and, responding to the exploratory reflex, moved into the dark section. The length of time (seconds) from when the animal was placed in the box to when it moved into the dark section is the latent period of the reaction.

The time spent by the animal in the light and dark chambers separately was recorded over a period of 120 s.

The selected animals were conditioned at fixed intervals of time after administration of the test material. For this purpose, an animal was placed in the light section of the box and after it had moved into the dark section a foot shock was applied through the metal mesh floor.

Conditioning was assessed 2 and 24 hours after application of the conditioning agent (the foot shock) in order to assess the state of the short-term and long-term memory respectively. For this purpose, an animal was placed in the light section of the box and the time spent by animals in the light and dark sections of the box was recorded over a period of 120 s, and also the duration of the latent period of the reaction and the number of (conditioned) animals which had not entered the dark section.

The results were assessed by comparing the length of the latent period of movement into the dark section of the box, the number of animals which had not entered the dark section (the conditioned specimens), and also the time spent in the dark and light sections of the box in the experiment (given a test drink) and the control (given a corresponding standard alcohol solution). The conditioned animals should not enter the preferable dark section or be there for only a short time, thus a reduction in the duration of the latent period of movement, an increase in the length of time spent in the dark chamber, or the very act of being in the dark section testifies to memory disruption and consequently to disruption of CNS function[39].

The results were processed using the Student method. Results with $P<0.05$ were considered reliable.

ECS.

Amnesia in the animals mice is created by application of an electroconvulsant shock (ECS) immediately (within 10 s) after development of PACR. An ECS is delivered via electrodes applied to the cornea of the eyes (15-20 mA, 200-500 ms).

Groups of Animals:

First Series of Experiments:

First group—control 1 (intact animals, conditioned),

Second group—method control 2 (physiological saline was administered to the animals and an ECS was applied immediately after conditioning), Third group—15 minutes before conditioning the preparation ampakine was administered to the animals in a dose of 0.025 mg/kg, after which an ECS was applied, Fourth group—15 minutes before conditioning the preparation ampakine was administered to the animals in a dose of 0.0025 mg/kg, after which an ECS was applied. The initial (before application of the ECS) number of animals in a group was 20. After application of the ECS it was from 11 to 16.

Second Series of Experiments:

First group—control 1 (intact animals, conditioned),

Second group—method control 2 (physiological saline was administered to the animals and an ECS was applied immediately after conditioning), Third group—15 minutes before conditioning the preparation Z-108a was administered to the animals in a dose of 0.025 mg/kg, after which an ECS was applied, Fourth group—15 minutes before conditioning the experimental compound preparation was administered to the animals in a dose of 0.025 mg/kg, after which an ECS was applied. The initial (before application of the ECS) number of animals in the groups was 20. After application of the ECS it was from 11 to 16.

Third Series of Experiments

First group—control 1 (intact animals, conditioned),

Second group—method control 2 (physiological saline was administered to the animals and an ECS was applied immediately after conditioning), Third group—15 minutes before conditioning the preparation ampakine was administered to the animals in a dose of 0.025 mg/kg, Fourth group—the preparation Z-108a was administered to the animals in a dose of 0.025 mg/kg, after which an ECS was applied, Fifth group—15 minutes before conditioning the experimental compound was administered to the animals in a dose of 0.025 mg/kg, after which an ECS was applied, Sixth group—the experimental compound was administered to the animals in a dose of 0.25 mg/kg, after which an ECS was applied.

The initial (before application of the ECS) number of animals in the groups was 10. After application of the ECS it was 9-7.

The test preparations were administered intra-peritoneally.

Results of the Investigation

The results are presented in Tables 1-3.

The effect of ampakine on implementation of PACR in an ECS amnesia model.

TABLE 1

| Parameter recorded, $M \pm m$ | Groups of animals | | | |
|---|---|---|---|---|
| | Control 1 | Control 2 | Experimental compound I, 0.025 mg/kg | Experimental compound II, 0.0025 mg/kg |
| 1 | 2 | 3 | 4 | 5 |
| Before conditioning | | | | |
| Latent period, s | $10.6 \pm 1.4$ | $10.1.1.8\pm$ | $9.8 \pm 1.6$ | $13.7 \pm 1.6$ |
| Time spent in light chamber, s | $26.2 \pm 1.9$ | $23.2 \pm 2.8$ | $16.6 \pm 2.7$ | $23.5 \pm 4.4$ |
| Time spent in dark chamber, s | $93.8 \pm 1.9$ | $87.9 \pm 9.7$ | $103.4 \pm 2.8$ | $96.5 \pm 4.3$ |
| 2 hours after conditioning | | | | |
| Latent period, s | $109.5 \pm 12.4$ | $51.9 \pm 12.4^*$ (t = 4.3) | $88.4 \pm 10.7^{**}$ (t = 2.2) | $70.3 \pm 8.5$ (t = 1.2) |
| Time spent in light chamber, s | $111.8 \pm 8.8$ | $54.0 \pm 10.3^*$ (t = 4.3) | $93.3 \pm 10.2^{}$ (t = 2.7) | $83.1 \pm 8.5^{}$ (t = 2.2) |
| Time spent in dark chamber, s | $8.2 \pm 8.8$ | $66.6 \pm 12.1^*$ (t = 3.9) | $26.6 \pm 9.2^{**}$ (t = 2.6) | $36.9 \pm 7.2$ (t = 1.9) |
| Number of animals conditioned, % | 90% | 10% | 50% | 46.6% |
| 24 hours after conditioning | | | | |
| Latent period, s | $109.5 \pm 12.4$ | $75.6 \pm 12.4$ (t = 1.7) | $64.8 \pm 10.7$ (t = 0.7) | $60.5 \pm 8.5$ (t = 0.7) |
| Time spent in light chamber, s | $111.1 \pm 1.8$ | $87.3 \pm 10.0^*$ (t = 2.4) | $96.6 \pm 8.0$ (t = 0.2) | $79.3 \pm 8.5$ (t = 0.6) |
| Time spent in dark chamber, s | $8.2 \pm 8.8$ | $32.7 \pm 3.6^*$ (t = 2.6) | $22.6 \pm 7.1$ (t = 1.3) | $40.7 \pm 8.3$ (t = 0.8) |
| Number of animals conditioned, % | 80% | 60% | 50% | 26.6% |

*$P \leq 0.05$ compared with control 1
**$P \leq 0.05$ compared with control 2

The results in Table 1 demonstrate: first, the adequacy of the model of creating amnesia by application of an ECS, and second that the experimental compounds exhibit nootropic activity in a dose of 0.25 mg/kg when tested 2 hours after conditioning, i.e. there is a positive effect on the short-term memory.

The Effect of the Test Preparations on Implementation of PACR in an ECS Amnesia Model is Shown in Table 2.

hours after conditioning), while when tested after 24 hours the number of conditioned animals increases on administration of these preparations, but the times virtually do not differ from the control. It is not possible to make a choice in favor of any particular compound, since there is no reliable difference between the experimental groups.

TABLE 2

| | Groups of animals | | | |
|---|---|---|---|---|
| Parameter recorded, M ± m 1 | Control 1 2 | Control 2 3 | Experimental compound I, 0.025 mg/kg 4 | Experimental compound II, 0.025 mg/kg 5 |
| Before conditioning | | | | |
| Latent period, s | 4.6 ± 1.4 | 8.8 ± 1.7 | 5.6 ± 1.2 | 4.8 ± 0.9 |
| Time spent in light chamber, s | 24.3 ± 6.7 | 26.3 ± 4.9 | 17.0 ± 2.7 | 37.5 ± 6.2.4 |
| Time spent in dark chamber, s | 95.7 ± 6.3 | 93.7 ± 4.9 | 103.4 ± 5.4 | 82.5 ± 6.2 |
| 2 hours after conditioning | | | | |
| Latent period, s | 115.3 ± 4.9 | 49.1 ± 10.4* (t = 6.0) | 65.2 ± 11.6 (t = 1.0) | 77.4 ± 11.7 (t = 1.8) |
| Time spent in light chamber, s | 115.3 ± 4.9 | 51.0 ± 8.3* (t = 7.1) | 98.5 ± 7.5** (t = 4.2) | 87.7 ± 2.6** (t = 3.6) |
| Time spent in dark chamber, s | 4.7 ± 4.7 | 69.0 ± 11.6* (t = 5.1) | 21.5 ± 11.8** (t = 2.9) | 32.3 ± 2.6** (t = 3.05) |
| Number of animals conditioned, % | 77.7% | 25% | 50% | 55.5% |
| 24 hours after conditioning | | | | |
| Latent period, s | 98.8 ± 10.3 | 59.9 ± 10.8* (t = 2.6) | 72.5 ± 11.8 (t = 0.8) | 79.7 ± 12.6 (t = 1.2) |
| Time spent in light chamber, s | 98.8 ± 9.6 | 86.6 ± 4.1 (t = 1.2) | 96.2 ± 11.1 (t = 1.0) | 96.4 ± 6.2 (t = 1.3) |
| Time spent in dark chamber, s | 8.2 ± 8.8 | 11.7 ± 4.0 (t = 0.4) | 23.8 ± 9.2 (t = 1.1) | 23.5 ± 6.1 (t = 1.6) |
| Number of animals conditioned, % | 80% | 37%% | 50% | 55.5% |

*P ≤ 0.05 compared with control 1
**P ≤ 0.05 compared with control 2

It follows from the results in the table that both test preparations reliably improve the short-term memory (2

The Effect of the Test Preparations on Implementation of PACR in an ECS Amnesia Model is Shown in Table 3.

TABLE 3

| | Groups of animals | | | | | |
|---|---|---|---|---|---|---|
| Parameter recorded, M ± m 1 | Control 1 2 | Control 2 3 | Experimental compound I, 0.025 mg/kg 4 | Experimental compound II, 0.025 mg/kg 5 | Experimental compound III, 0.025 mg/kg 6 | Experimental compound IV, 0.025 mg/kg 7 |
| Before conditioning | | | | | | |
| Latent period, s | 5.35 ± 0.3 | 6.9 ± 0.9 | 6.9 ± 0.9 | 6.8 ± 0.7 | 7.4 ± 0.9 | 5.0 ± 0.6 |
| Time spent in light chamber, s | 19.85 ± 2.8 | 84.5 ± 3.0 | 28.0 ± 2.38 | 7.8 ± 1.6 | 22.7 ± 2.4 | 14.5 ± 1.6 |
| Time spent in dark chamber, s | 101.15 ± 1.6 | 35.5 ± 3.0 | 92.0 ± 2.4 | 112.2 ± 1.5 | 97.3 ± 2.4 | 105.4 ± 1.4 |
| After 2 hours | | | | | | |
| Latent period, s | 117.65 ± 2.8 | 33.7 ± 4.7* (t = 6.6) | 60.6 ± 12.3 (t = 2.0) | 69.4 ± 11.1** (t = 2.9) | 69.2 ± 3.0** (t = 6.4) | 41.2 ± 10.8 (t = 0.6) |
| Time spent in light chamber, s | 117.65 ± 2.8 | 39.0 ± 4.9* (t = 10.1) | 81.5 ± 10.4** (t = 3.7) | 88.4 ± 7.5** (t = 5.5) | 84.0 ± 13.0** (t = 3.2) | 41.8 ± 10.4 (t = 0.2) |

TABLE 3-continued

| Parameter recorded, M ± m | Groups of animals | | | | | |
|---|---|---|---|---|---|---|
| | Control 1 | Control 2 | Experimental compound I, 0.025 mg/kg | Experimental compound II, 0.025 mg/kg | Experimental compound III, 0.025 mg/kg | Experimental compound IV, 0.025 mg/kg |
| | 2 | 3 | 4 | 5 | 6 | 7 |
| Time spent in dark chamber, s | 1.35 ± 7.2 | 85.0 5.48* (t = 9.2) | 38.5 ± 11.07** (t = 3.8) | 31.6 ± 9.7** (t = 4.8) | 36.0 ± 13.0** (t = 3.5) | 78.2 ± 10.6 (t = 0.57) |
| Number of animals conditioned, % | 90 | 0 | 44 | 28.5 | 44 | 33 |
| After 24 hours | | | | | | |
| Latent period, s | 98.1 ± 2.8 | 58.2 ± 13.2* (t = 2.9) | 52.9 ± 13.0 (t = 0.3) | 30.0 ± 11.8 (t = 1.5) | 77.1 ± 13.8 (t = 0.9) | 37.2 ± 11.9 (t = 1.2) |
| Time spent in light chamber, s | 110.15 ± 2.8 | 59.5 ± 13.8* (t = 3.6) | 98.3 ± 4.7** (t = 2.7) | 61.4 ± 9.4 (t = 0.1) | 95.6 ± 8.3** (t = 3.2) | 50.4 ± 11.9 (t = 0.5) |
| Time spent in dark chamber, s | 9.8 ± 7.0 | 60.5 ± 8.6* (t = 4.6) | 21.7 ± 4.7** (t = 3.9) | 58.6 ± 12.5 (t = 0.12) | 24.4 ± 4.6** (t = 3.7) | 69.6 ± 11.6 (t = 0.6) |
| Number of animals conditioned, % | 50 | 14.2 | 11.1 | 14.3 | 55 | 33 |

*$P \leq 0.05$ compared with control 1
**$P \leq 0.05$ compared with control 2

The results presented in Table 3 show that the experimental compounds exhibit nootropic activity, which is manifested after 2 and 24 hours, both in regard to the number of conditioned animals, and also in relation to the times spent in the dark and light chambers. Experimental compound III is the most active in this model of amnesia, its effect being stable in both series of experiments, with the anti-amnesic effect registered both in relation to the number of conditioned animals and also in relation to the time characteristics, and being manifested in relation to both short-term and long-term memory.

INDUSTRIAL APPLICABILITY

The invention relates to novel derivatives of N,N'-substituted 3,7-diazabicyclo[3.3.1]nonanes which have pharmacological activity and may be used for the treatment of neurodegenerative pathologies.

The invention claimed is:

1. A pharmaceutical composition, the composition comprising a compound of a general formula 1, or a pharmacologically acceptable acid or salt thereof:

(1)

(HM)

wherein:
X is a carbonyl group, or a methylene bridge;
$R_1$ and $R'_1$ are identical or different, and each independently is H, $C_1$-$C_6$ alkyl, or $C_1$-$C_{10}$ alkoxy;
$R_2$ is selected from the group consisting of general formulae (1.1a), (1.2a), (1.3a), and (1.4a):

$R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, $R'_{10}$, $R_{11}$, $R'_{11}$, $R_{15}$ and $R'_{15}$ are identical or different, and each independently is H, $C_1$-$C_6$ alkyl, or $C_1$-$C_{10}$ alkoxy;

$R_{12}$ is $C_1$-$C_6$ alkyl;

$R_{13}$ and $R_{13}'$ are identical or different, and each independently is H, $C_1$-$C_6$ alkyl, $C_1$-$C_{10}$ alkoxy, hydroxy, halogen, amino, nitro group, nitrile, acyl, or aryl;

Z is N or CH;

E is N, or a group having a general formula:

$$-(C)_n-$$
with $R_{14}$ on C wherein: n equals 1, 2, or 3;

$R_{14}$ is H, $C_1$-$C_6$ alkyl, $C_1$-$C_{10}$ alkoxy, or hydroxyl;

Y is $-(CR_{16}R'_{16})_m-$, wherein m equals 1, 2, or 3;

$R_{16}$ and $R'_{16}$ are identical or different, and each independently is H, $C_1$-$C_6$ alkyl, or $C_1$-$C_{10}$ alkoxy.

2. The composition of claim 1, wherein said compound has a general formula (1.1):

3. The composition of claim 1, wherein said compound has a general formula (1.2):

4. The composition of claim 1, wherein said compound has a general formula (1.3):

5. The composition of claim 1, wherein said compound has a general formula (1.4):

6. The composition of claim 2, wherein said compounds are:
  6-[4-methoxy-3-(1H-pyrazol-1-ylmethyl)benzyl]-1,11-dimethyl-3,6,9-triazatricyclo [7.3.1.1$^{3,11}$]tetradecane-4,8,12-trione;
  6-[4-methoxy-3-(3,5-dimethyl-1H-pyrazol-1-ylmethyl)-benzyl]-1,11-dimethyl-3,6,9-triazatricyclo[7.3.1.1$^{3,11}$]tetra-decane-4,8,12-trione; or
  6-[4-methoxy-3-(2-methyl-1H-imidazol-1-ylmethyl)benzyl]-1,11-dimethyl-3,6,9-triazatricyclo[7.3.1.1$^{3,11}$]tetradecane-4,8,12-trione.

7. The composition of claim 3, wherein said compound is:
  6-[4-methoxy-3-(piperidin-1-ylmethyl)benzyl]-1,11-dimethyl-3,6,9-triazatricyclo[7.3.1.1$^{3,11}$]tetradecane-4,8,12-trione.

8. The composition of claim 4, wherein said compound is:
  6-{3-[(2-fluorophenoxy)methyl]-4-methoxybenzyl}-1,11-dimethyl-3,6,9-triazatricyclo[7.3.1.1$^{3,11}$]tetradecane-4,8,12-trione.

9. The composition of claim 5, wherein said compound is:
  6-{4-methoxy-3-[(1,3-thiazol-2-ylamino)methyl]benzyl}-1,11-dimethyl-3,6,9-triazatricyclo [7.3.1.1$^{3,11}$]tetradecane-4,8,12-trione.

10. A method of modulating AMPA. (2-amino-3-(3-hydroxy-5-methylisoxazol-4-yl)propionic acid) receptor activity, the method comprising: administering a therapeutically effective amount of the compound of claim 1 to a patient in need thereof.

11. A method of treating a human disorder, the method comprising administering a therapeutically effective amount of the compound of claim 1 to a patient in need of treating or preventing a disorder selected from the group consisting of:
  neurodegenerative disorders;
  attention and memory disorders;
  behavioral disturbances associated with neurodegenerative disorders;
  deficit psychiatric disorders with functional psychiatric disturbances;
  Attention Deficit Hyperactivity Disorder (ADHD) syndrome,
  hypersomnia and narcolepsy symptoms; and
  mood disorders.

12. The method of claim 10, wherein the therapeutically effective amount of the compound of claim 1 is administered to a healthy person and in an amount effective to enhance memory, attention or learning.

13. The method of claim 10, wherein the therapeutically effective amount of the compound of claim 1 is administered to a patient prior to a surgical intervention under anesthesia or a neurosurgical intervention, in an amount effective to protect against damage to the central nervous system from said intervention.

* * * * *